United States Patent
Olsson et al.

(10) Patent No.: US 12,202,854 B2
(45) Date of Patent: Jan. 21, 2025

(54) PROCESS FOR THE PRODUCTION OF DATH AND INTERMEDIATES THEREOF

(71) Applicant: Galderma Holding SA, Zug (CH)

(72) Inventors: Johan Olsson, Bromma (SE); Kristoffer Bergman, Stockholm (SE)

(73) Assignee: Galderma Holding SA, Zug (CH)

( * ) Notice: Subject to any disclaimer, the term of this patent is extended or adjusted under 35 U.S.C. 154(b) by 0 days.

(21) Appl. No.: 17/745,471

(22) Filed: May 16, 2022

(65) Prior Publication Data
US 2022/0389044 A1 Dec. 8, 2022

Related U.S. Application Data

(60) Provisional application No. 63/189,938, filed on May 18, 2021.

(51) Int. Cl.
 *C07H 3/04* (2006.01)
 *C07H 1/00* (2006.01)
 *C07H 1/06* (2006.01)

(52) U.S. Cl.
 CPC ............... *C07H 3/04* (2013.01); *C07H 1/00* (2013.01); *C07H 1/06* (2013.01)

(58) Field of Classification Search
 CPC ... C07H 1/00; C07H 3/04; C07H 5/06; C07H 1/06
 See application file for complete search history.

(56) References Cited

PUBLICATIONS

Hanessian, S.; Plessas, N. R. "The Reaction of O-Benzylidene Sugars with N-Bromosuccinimide. II. Scope and Synthetic Utility in the 4,6-O-Benzylidenehexopyranoside Series" 1969, Journal of Organic Chemistry, vol. 34, pp. 1035-1044. (Year: 1969).*
Sarpe, V.A.; Kulkarni, S. S. "Desymmetrization of trehalose via regioselective DIBAL reductive ring opening of benzylidene and substituted benzylidene acetals" 2013, Organic and Biomolecular Chemistry, vol. 11, pp. 6460-6465. (Year: 2013).*
Liav, A.; Goren, M. B. "Concerning 2,3,4,2',3',4'-hexa-O-acetyl-6,6'-diamino-6,6'-dideoxy-α,α-trehalose" 1980, Carbohydrate Research, vol. 87, pp. 278-293. (Year: 1980).*
Shimizu, Y.; et al. "Cleavage of unactivated amide bonds by ammonium salt-accelerated hydrazinolysis" 2014, Chemical Communications, vol. 50, pp. 12623-12625. (Year: 2014).*
Kizjakina, K.; et al. "Cationic glycopolymers for the delivery of pDNA to human dermal fibroblasts and rat mesenchymal stem cells" 2012, Biomaterials, vol. 33, pp. 1851-1862 (Year: 2012).*
Hema, K.; et al. "Crystal-to-Crystal Synthesis of Helically Ordered Polymers of Trehalose by Topochemical Polymerization" 2020, Angew. Chem. Int. Ed., vol. 59, pp. 2897-2903. (Year: 2020).*
Wuts, P. G.; Greene, T. W.; Greene's Protective Groups in Organic Synthesis, Fourth Edition, 2007. (Year: 2007).*
Hui, Y.; et al. "Convenient Divergent Synthesis of a Library of Trehalosamine Analogues" 2002, Org Lett., vol. 4, pp. 2245-2248. (Year: 2002).*
Garcia Fernandez, J.M., et al., "Isothiocyanates and cyclic thiocarbamates of alpha,alpha'-trehalose, sucrose, and cyclomaltooligosaccharides," Carbohydrate Research 268:57-71 (1995) (15 pages).
Kurita, K., et al., "Synthetic Carbohydrate Polymers Containing Trehalose Residues in the Main Chain: Preparation and Characteristic Properties," Macromolecules 27:7544-7549 (1994) (6 pages).
Srinivasachari, S., et al., "Trehalose Click Polymers Inhibit Nanoparticle Aggregation and Promote pDNA Delivery in Serum," J. Am. Chem. Soc. 128:8176-8184 (2006) (9 pages).
Hui et al., "Convenient Divergent Synthesis of a Library of Trehalosamine Analogues", Organic Letters, vol. 4, No. 13, XP055944316, Jun. 1, 2002, pp. 2245-2248, retrieved from: https://pubs.acs.org/doi/pdf/10.1021/ol026095m.
International Search Report and Written Opinion on PCT Appl. Ser. No. PCT/IB2022/054548 dated Aug. 1, 2022 (15 pages).
Reineke et al., "Structural Effects of Carbohydrate-Containing Polycations on Gene Delivery. 1. Carbohydrate Size and Its Distance from Charge Centers", Bioconjugate Chemistry, vol. 14, No. 1, XP055907379, Jan. 1, 2003, pp. 247-254.
Rose et al., "Synthesis and biological evaluation of trehalose analogs as potential inhibitors of mycobacterial cell wall biosynthesis", Carbohydrate Research, vol. 337, No. 2, XP004334241, Feb. 1, 2002, pp. 105-120.
Tan et al., "Synthesis and antioxidant ability of 6,6'-diamino-6,6'-dideoxytrehalose", Bioorganic Chemistry, vol. 74, XP085176470, Jul. 20, 2017, pp. 66-71.

* cited by examiner

*Primary Examiner* — Eric Olson
*Assistant Examiner* — Benjamin M Brandsen
(74) *Attorney, Agent, or Firm* — Foley & Lardner LLP

(57) ABSTRACT

The present technology is directed to methods of producing 6,6'-diamino-6,6'-dideoxy-trehalose ("DATH") or a salt thereof. The methods include optionally protecting one or more hydroxyl groups of D-trehalose and converting the primary hydroxyl groups of D-trehalose to produce DATH or a salt thereof through use of a halogen, azide, and/or protected amine. The present technology is also directed to intermediate products of the methods.

15 Claims, No Drawings

PROCESS FOR THE PRODUCTION OF DATH AND INTERMEDIATES THEREOF

CROSS-REFERENCE TO RELATED APPLICATIONS

This application claims priority under 35 U.S.C. § 119(e) to U.S. Provisional Application No. 63/189,938, filed May 18, 2021, which is hereby incorporated by reference in its entirety.

TECHNICAL FIELD

The invention relates to a process for making 6,6'-diamino-6,6'-deoxy-trehalose ("DATH") or salts thereof and intermediate compounds produced by the process.

BACKGROUND

DATH is a small molecule commonly used as a cross-linker or monomer in polymer synthesis. DATH can be manufactured and stored as the uncharged amine or its salt form.

SUMMARY

The present technology is directed to methods of producing DATH or salts thereof and, in particular, producing DATH or salts thereof using trehalose as a starting material.

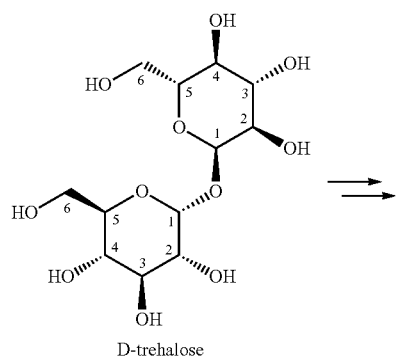

D-trehalose

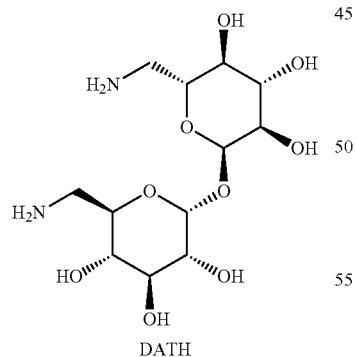

DATH

In one aspect, the present technology is directed to a method of producing DATH or a salt thereof including (1) optionally protecting and/or replacing one or more primary and/or secondary hydroxyl groups of D-trehalose to provide a D-trehalose derivative; (2) protecting one or more primary and/or secondary hydroxyl groups of the D-trehalose or the D-trehalose derivative to provide an intermediate 1A or replacing the primary hydroxyl groups of the D-trehalose or the D-trehalose derivative with halides to provide intermediate 1B; (3) replacing the primary hydroxyl protected groups with protected amines or with azides to provide intermediate 2, or replacing the halides with protected amines or with azides to provide intermediate 2; and (4) converting the intermediate 2 to DATH or a salt thereof.

In another aspect, the present technology is direct to a method of producing DATH or a salt thereof including (1) optionally reacting D-trehalose with one or more protecting groups to provide a D-trehalose derivative; (2) reacting primary hydroxyl groups at carbon 6 of each monosaccharide of the D-trehalose or the D-trehalose derivative and 4-nitrobenzenesulfonyl-LG to provide intermediate 1A comprising 4-nitrobenzenesulfonyl hydroxyl protected groups, or reacting the primary hydroxyl groups of the D-trehalose or the D-trehalose derivative and a halogen to provide intermediate 1B comprising halide groups; (3) reacting the 4-nitrobenzenesulfonyl hydroxyl protected groups and potassium phthalimide, benzyl amine, ammonia, or $NaN_3$ to provide intermediate 2A, or reacting the halide groups and potassium phthalimide, benzyl amine, or $NaN_3$ to provide intermediate 2B; and (4) converting the intermediate 2A or the intermediate 2B to DATH or a salt thereof; wherein LG represents a leaving group.

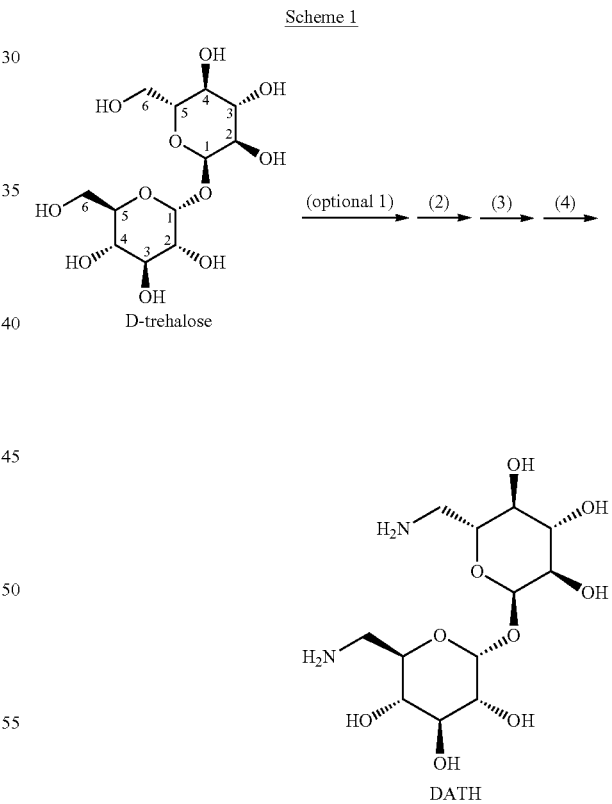

Scheme 1

In any embodiment, the methods may include one or more additional steps. For example, one or more steps may occur before and/or after step 1, step 2, step 3, and/or step 4.

The present technology is also directed to intermediate products prepared during the method of producing DATH. In one aspect, the present technology is directed to a compound of formula II:

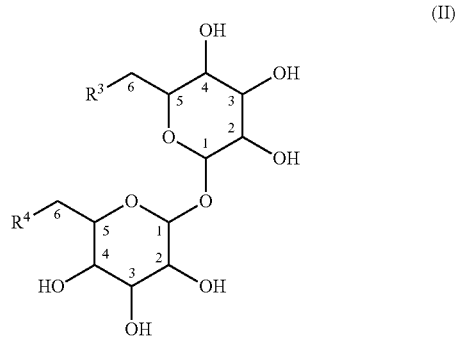
(II)

wherein R³ and R⁴ are independently selected from the group consisting of I or $N_3$.

DETAILED DESCRIPTION

The following terms are used throughout as defined below.

As used herein and in the appended claims, singular articles such as "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

The term "leaving group" or "LG" refers to group or atoms readily displaceable by a nucleophile, such as an amine, alcohol, phosphorus, or thiol nucleophile or their respective anions. Such leaving groups are well known and include carboxylates, N-hydroxysuccinimide, N-hydroxybenzotriazole, halogen (halides including Cl⁻, Br⁻, and I⁻), triflates, tosylates, mesylates, alkoxy, thioalkoxy, phosphinates, phosphonates, p-nitrobenzensulphonyloxy, and the like. In addition, the term "leaving group" or "LG" is meant to encompass leaving group precursors (i.e., moieties that can easily be converted to a leaving group upon simply synthetic procedures such as alkylation, oxidation or protonation). Such leaving group precursors and methods for converting them to leaving groups are well known to those of ordinary skill in the art.

The term "protecting group" or "PG" has the meaning conventionally associated with it in organic synthesis, i.e., a group that selectively blocks one or more reactive sites in a multifunctional compound such that a chemical reaction can be carried out selectively on another unprotected reactive site and such that the group can readily be removed after the selective reaction is complete. Non-limiting embodiments of functional groups that can be masked with a protecting group include an amine, hydroxy, thiol, carboxylic acid, and aldehyde. For example, a hydroxy protected form is where at least one of the hydroxy groups present in a compound is protected with a hydroxy protecting group. A variety of protecting groups are disclosed, for example, Greene's Protective Groups in Organic Synthesis, Fifth Edition, Wiley (2014), incorporated herein by reference in its entirety. For additional background information on protecting group methodologies (materials, methods and strategies for protection and deprotection) and other synthetic chemistry transformations useful in producing the compounds described herein, see in R. Larock, Comprehensive organic Transformations, VCH Publishers (1989); Greene's Protective Groups in Organic Synthesis, Fifth Edition, Wiley (2014); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995). These references are incorporated herein by reference in their entirety.

In general, "substituted group" refers to an organic group as defined below (e.g., an alkyl group) in which one or more bonds to a hydrogen atom contained therein are replaced by a bond to non-hydrogen or non-carbon atoms. Substituted groups also include groups in which one or more bonds to a carbon(s) or hydrogen(s) atom are replaced by one or more bonds, including double or triple bonds, to a heteroatom. Thus, a substituted group is substituted with one or more substituents, unless otherwise specified. In any embodiment, a substituted group is substituted with 1, 2, 3, 4, 5, or 6 substituents. Examples of substituent groups include: halogens (i.e., F, Cl, Br, and I); $CF_3$; hydroxyls; alkoxy, alkenoxy, aryloxy, aralkyloxy, heterocyclyl, heterocyclylalkyl, heterocyclyloxy, and heterocyclylalkoxy groups; carbonyls (oxo); carboxylates; esters; urethanes; oximes; hydroxylamines; alkoxyamines; aralkoxyamines; thiols; sulfides; sulfoxides; sulfones; sulfonyls; pentafluorosulfanyl (i.e., $SF_5$), sulfonamides; amines; N-oxides; hydrazines; hydrazides; hydrazones; azides; amides; amines; ureas; amidines; guanidines; enamines; imides; isocyanates; isothiocyanates; cyanates; thiocyanates; imines; nitro groups; nitriles (i.e., CN); and the like.

Substituted ring groups such as substituted cycloalkyl, aryl, heterocyclyl and heteroaryl groups also include rings and ring systems in which a bond to a hydrogen atom is replaced with a bond to a carbon atom. Therefore, substituted cycloalkyl, aryl, heterocyclyl and heteroaryl groups may also be substituted The term "alkyl" refers to a group, whether alone or as part of another group (e.g., in dialkylamino), encompasses straight and branched chain aliphatic groups (i.e., saturated hydrocarbyl chains), and, unless otherwise indicated, has 1-10, alternatively 1-8, or alternatively 1-6 alkyl carbon atoms. Preferred alkyl groups include, without limitation, methyl, ethyl, propyl, isopropyl, butyl, isobutyl, sec-butyl, tert-butyl, pentyl, and hexyl. Unless otherwise indicated, the alkyl group is optionally substituted with 1, 2, or 3, preferably 1 or 2, more preferably 1, substituents that are compatible with the compounds, monomers, and polymers described herein. Representative substituted alkyl groups may be substituted one or more times with substituents such as those listed above, and include without limitation haloalkyl (e.g., trifluoromethyl), hydroxyalkyl, thioalkyl, amino-alkyl, alkylaminoalkyl, dialkylaminoalkyl, alkoxyalkyl, carboxyalkyl, and the like. In any embodiment, the alkyl group is unsubstituted.

Alkenyl groups include straight and branched chain alkyl groups as defined above, except that at least one double bond exists between two carbon atoms. Alkenyl groups have from 2 to 12 carbon atoms, and typically from 2 to 10 carbons or, In any embodiment, from 2 to 8, 2 to 6, or 2 to 4 carbon atoms. In any embodiment, the alkenyl group has one, two, or three carbon-carbon double bonds. Examples include, but are not limited to vinyl, allyl, —CH=CH(CH$_3$), —CH=C(CH$_3$)$_2$, —C(CH$_3$)=CH$_2$, —C(CH$_3$)=CH(CH$_3$), —C(CH$_2$CH$_3$)=CH$_2$, among others. Representative substituted alkenyl groups may be mono-substituted or substituted more than once, such as, but not limited to, mono-, di- or tri-substituted with substituents such as those listed above.

The term "(hetero)cycloalkyl" refers to cycloalkyl and heterocycloalkyl groups.

The term "cycloalkyl" refers to saturated cyclic hydrocarbon groups. Unless otherwise indicated, the cycloalkyl group has 3 to 12 ring carbon atoms, alternatively 3 to 8 ring carbon atoms, or alternatively 3 to 6 ring carbon atoms. Preferred cycloalkyl groups include, without limitation, cyclopropyl, cyclobutyl, cyclopentyl, cyclopentenyl, and cyclohexyl. Unless otherwise indicated, the cycloalkyl group is optionally substituted with 1, 2, or 3, preferably 1 or 2, more preferably 1 alkyl group. In any embodiment, the alkyl group may include 1-6 carbon atoms, preferably the alkyl group is unsubstituted and includes 1-4 carbon atoms. In any embodiment, the cycloalkyl group is unsubstituted.

The term "heterocycloalkyl" as used herein refers to non-aromatic ring compounds containing 5 or more ring members, of which at least three are carbon atoms and at least one is a nitrogen atom. In any embodiment, the heterocyclyl group contains 1 or 2 heteroatoms. In any embodiment, the heterocyclyl group may include at least 4 or at least 5 carbon atoms. Typically, the heterocycloalkyl group is unsubstituted.

The term "(hetero)aryl" refers to aryl and heteroaryl groups.

Aryl groups are cyclic aromatic hydrocarbons that do not contain heteroatoms. Aryl groups herein include monocyclic, bicyclic and tricyclic ring systems. Thus, aryl groups include, but are not limited to, phenyl, azulenyl, heptalenyl, biphenyl, fluorenyl, phenanthrenyl, anthracenyl, indenyl, indanyl, pentalenyl, and naphthyl groups. In any embodiment, aryl groups contain 6-14 carbons, and in others from 6 to 12 or even 6-10 carbon atoms in the ring portions of the groups. In any embodiment, the aryl groups are phenyl or naphthyl. Although the phrase "aryl groups" includes groups containing fused rings, such as fused aromatic-aliphatic ring systems (e.g., indanyl, tetrahydronaphthyl, and the like), it does not include aryl groups that have other groups, such as alkyl or halo groups, bonded to one of the ring members. Rather, groups such as tolyl are referred to as substituted aryl groups. Representative substituted aryl groups may be mono-substituted or substituted more than once. For example, monosubstituted aryl groups include, but are not limited to, 2-, 3-, 4-, 5-, or 6-substituted phenyl or naphthyl groups, which may be substituted with substituents such as those listed above.

Heteroaryl groups are aromatic ring compounds containing 5 or more ring members, of which, one or more is a heteroatom such as, but not limited to, N, O, and S. Heteroaryl groups include, but are not limited to, groups such as pyrrolyl, pyrazolyl, triazolyl, tetrazolyl, oxazolyl, isoxazolyl, thiazolyl, pyridinyl, pyridazinyl, pyrimidinyl, pyrazinyl, thiophenyl, benzothiophenyl, furanyl, benzofuranyl, indolyl, azaindolyl(pyrrolopyridinyl), indazolyl, benzimidazolyl, imidazopyridinyl(azabenzimidazolyl), pyrazolopyridinyl, triazolopyridinyl, benzotriazolyl, benzoxazolyl, benzothiazolyl, benzothiadiazolyl, imidazopyridinyl, isoxazolopyridinyl, thianaphthyl, purinyl, xanthinyl, adeninyl, guaninyl, quinolinyl, isoquinolinyl, tetrahydroquinolinyl, quinoxalinyl, and quinazolinyl groups. Heteroaryl groups include fused ring compounds in which all rings are aromatic such as indolyl groups and include fused ring compounds in which only one of the rings is aromatic, such as 2,3-dihydro indolyl groups. Although the phrase "heteroaryl groups" includes fused ring compounds, the phrase does not include heteroaryl groups that have other groups bonded to one of the ring members, such as alkyl groups. Rather, heteroaryl groups with such substitution are referred to as "substituted heteroaryl groups." Representative substituted heteroaryl groups may be substituted one or more times with various substituents such as those listed above.

Alkoxy groups are hydroxyl groups (—OH) in which the bond to the hydrogen atom is replaced by a bond to a carbon atom of a substituted or unsubstituted alkyl group as defined above. Examples of linear alkoxy groups include but are not limited to methoxy, ethoxy, propoxy, butoxy, pentoxy, hexoxy, and the like. Examples of branched alkoxy groups include but are not limited to isopropoxy, sec-butoxy, tert-butoxy, isopentoxy, isohexoxy, and the like. Examples of cycloalkoxy groups include but are not limited to cyclopropyloxy, cyclobutyloxy, cyclopentyloxy, cyclohexyloxy, and the like. Representative substituted alkoxy groups may be substituted one or more times with substituents such as those listed above.

The terms "alkanoyl" and "alkanoyloxy" as used herein can refer, respectively, to —C(O)-alkyl groups and —O—C(O)-alkyl groups, each containing 2-5 carbon atoms. Similarly, "aryloyl" and "aryloyloxy" refer to —C(O)-aryl groups and —O—C(O)-aryl groups.

The terms "aryloxy" and "arylalkoxy" refer to, respectively, a substituted or unsubstituted aryl group bonded to an oxygen atom and a substituted or unsubstituted aralkyl group bonded to the oxygen atom at the alkyl. Examples include but are not limited to phenoxy, naphthyloxy, and benzyloxy. Representative substituted aryloxy and arylalkoxy groups may be substituted one or more times with substituents such as those listed above.

The term "carboxylate" as used herein refers to a —COOH group or its ionized form —COO$^-$.

The term "ester" as used herein refers to —COOR$^{70}$ and —C(O)O-G groups. R$^{70}$ is a substituted or unsubstituted alkyl, cycloalkyl, alkenyl, alkynyl, aryl, aralkyl, heterocyclylalkyl or heterocyclyl group as defined herein. G is a carboxylate protecting group. Carboxylate protecting groups are well known to one of ordinary skill in the art. An extensive list of protecting groups for the carboxylate group functionality may be found in Protective Groups in Organic Synthesis, Greene, T. W.; Wuts, P. G. M., John Wiley & Sons, New York, NY, (3rd Edition, 1999) which can be added or removed using the procedures set forth therein and which is hereby incorporated by reference in its entirety and for any and all purposes as if fully set forth herein.

The term "amide" (or "amido") includes C- and N-amide groups, i.e., —C(O)NR$^{71}$R$^{72}$, and —NR$^{71}$C(O)R$^{72}$ groups, respectively. R$^{71}$ and R$^{72}$ are independently hydrogen, or a substituted or unsubstituted alkyl, alkenyl, alkynyl, cycloalkyl, aryl, aralkyl, heterocyclylalkyl or heterocyclyl group as defined herein. Amido groups therefore include but are not limited to carbamoyl groups (—C(O)NH$_2$) and formamide groups (—NHC(O)H). In any embodiment, the amide is —NR$^{71}$C(O)—(C$_{1-5}$ alkyl) and the group is termed "carbonylamino," and in others the amide is —NHC(O)-alkyl and the group is termed "alkanoylamino."

The term "nitrile" or "cyano" as used herein refers to the —CN group.

The term "amine" (or "amino") as used herein refers to —NR$^{75}$R$^{76}$ groups, wherein R$^{75}$ and R$^{76}$ are independently hydrogen, or a substituted or unsubstituted alkyl, alkenyl, alkynyl, cycloalkyl, aryl, aralkyl, heterocyclylalkyl or heterocyclyl group as defined herein. In any embodiment, the amine is alkylamino, dialkylamino, arylamino, or alkylarylamino. In other embodiments, the amine is NH$_2$, methylamino, dimethylamino, ethylamino, diethylamino, propylamino, isopropylamino, phenylamino, or benzylamino.

The term "halogen" or "halo" as used herein refers to bromine, chlorine, fluorine, or iodine. In any embodiment, the halogen is fluorine. In other embodiments, the halogen is chlorine or bromine.

The term "hydroxyl" as used herein can refer to —OH or its ionized form, A "hydroxyalkyl" group is a hydroxyl-substituted alkyl group, such as HO—CH$_2$—.

The term "imide" refers to —C(O)NR$^{98}$C(O)R$^{99}$, wherein R$^{98}$ and R$^{99}$ are each independently hydrogen, or a substituted or unsubstituted alkyl, cycloalkyl, alkenyl, alkynyl, aryl aralkyl, heterocyclyl or heterocyclylalkyl group as defined herein.

The term "imine" refers to —CR$^{100}$(NR$^{101}$) and —N(CR$^{100}$R$^{101}$) groups, wherein R$^{1o}$ $^{o}$ and R$^{101}$ are each independently hydrogen or a substituted or unsubstituted alkyl, cycloalkyl, alkenyl, alkynyl, aryl aralkyl, heterocyclyl or heterocyclylalkyl group as defined herein, with the proviso that R$^{100}$ and R$^{101}$ are not both simultaneously hydrogen.

The term "nitro" as used herein refers to an —NO$_2$ group.

Groups described herein having two or more points of attachment (i.e., divalent, trivalent, or polyvalent) within the compound of the present technology are designated by use of the suffix, "ene." For example, divalent alkyl groups are alkylene groups, divalent cycloalkyl groups are cycloalkylene groups, and so forth. Substituted groups having a single point of attachment to the compound of the present technology are not referred to using the "ene" designation. Thus, e.g., chloroethyl is not referred to herein as chloroethylene.

As used herein, "substantially free" refers to less than about 2 wt % of the specified component based on the total weight of the composition. In any embodiment, the composition may include less than about 1 wt %, less than about 0.5 wt %, or less than about 0.1 wt %. In any embodiment, the composition may free of detectable amounts of the component. For example, the composition may be free of detectable amounts of NMP.

In general, "substitution reaction" refers to an S$_N$1 or S$_N$2 reactions. The S$_N$1 reaction is a substitution reaction in which the rate-determining step is unimolecular and involves a carbocation intermediate i.e., two step reaction. It is commonly seen in reactions of secondary or tertiary alkyl halides. Conversely, the S$_N$2 reaction is a type of substitution reaction in which one bond is broken and one bond is formed synchronously, i.e., in one step, so two reacting species are involved in the slow (rate-determining) step. The reaction is commonly seen in reactions of primary or secondary alkyl halides.

In the schemes provided herein, the indication of an arrow in a reaction can indicate a single reaction or two or more reactions. The reactions may occur as a one-pot reaction or a two or more pot reaction.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 atoms refers to groups having 1, 2, or 3 atoms. Similarly, a group having 1-5 atoms refers to groups having 1, 2, 3, 4, or 5 atoms, and so forth.

Those of skill in the art will appreciate that compounds of the present technology may exhibit the phenomena of tautomerism, conformational isomerism, geometric isomerism and/or stereoisomerism. As the formula drawings within the specification and claims can represent only one of the possible tautomeric, conformational isomeric, stereochemical or geometric isomeric forms, it should be understood that the present technology encompasses any tautomeric, conformational isomeric, stereochemical and/or geometric isomeric forms of the compounds having one or more of the utilities described herein, as well as mixtures of these various different forms.

"Tautomers" refers to isomeric forms of a compound that are in equilibrium with each other. The presence and concentrations of the isomeric forms will depend on the environment the compound is found in and may be different depending upon, for example, whether the compound is a solid or is in an organic or aqueous solution. For example, in aqueous solution, guanidines may exhibit the following isomeric forms in protic organic solution, also referred to as tautomers of each other:

Because of the limits of representing compounds by structural formulas, it is to be understood that all chemical formulas of the compounds described herein represent all tautomeric forms of compounds and are within the scope of the present technology.

In one aspect, the present technology provides a method of producing DATH or a salt thereof including (1) optionally protecting and/or replacing one or more primary and/or secondary hydroxyl groups of D-trehalose to provide a D-trehalose derivative; (2) protecting one or more primary and/or secondary hydroxyl groups of the D-trehalose or the D-trehalose derivative to provide an intermediate 1A or replacing the primary hydroxyl groups of the D-trehalose or the D-trehalose derivative with halides to provide intermediate 1B; (3) replacing the primary hydroxyl protected groups with protected amines or with azides to provide intermediate 2, or replacing the halides with protected amines or with azides to provide intermediate 2; and (4) converting the intermediate 2 to DATH or a salt thereof.

In some embodiments, the method includes (1) protecting and/or replacing one or more primary and/or secondary hydroxyl groups of D-trehalose to provide a D-trehalose derivative occurs. In some embodiment, step (1) includes protecting the primary hydroxyl groups at carbon 6 of each monosaccharide of the D-trehalose occurs prior to step (2) (e.g., Scheme 2A). In any embodiment, step (1) includes protecting the secondary hydroxyl groups of each monosaccharide of the D-trehalose (e.g., Scheme 2B). In any embodiment, step (1) includes protecting the primary and the secondary hydroxyl groups of each monosaccharide of the D-trehalose (e.g., Scheme 2C). The protecting groups in any of the Schemes 2A-2C may be any known hydroxyl protecting group. In any embodiment, the protecting groups may be an ether and/or silyl ether protecting group. In any embodiment, the protecting groups may include tosyl, mesyl, 4-nitrobenzenesulfonyl, acetyl, benzoyl, benzyl, methoxyethoxymethyl ether, dimethoxytrityl, methoxymethyl ether, methoxytrityl, p-methoxybenzyl ether, p-methoxyphenyl ether, methylthiomethyl ether, pivaloyl, tetrahydropyranyl, tetrahydrofuran, trityl, trimethylsilyl, t-butylisopropylsilyl, tri-isopropylsilyloxymethyl, triisopropylsilyl, methyl ethers, ethoxyethyl ethers, or combinations of two or more thereof. In any embodiment, the protecting groups may include tosyl, acetyl, trityl, or combinations of two or more thereof. Protecting group A and B may be the same or different.

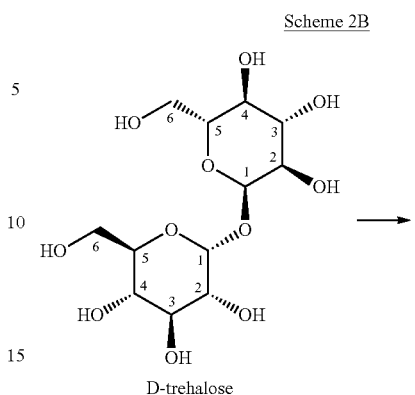

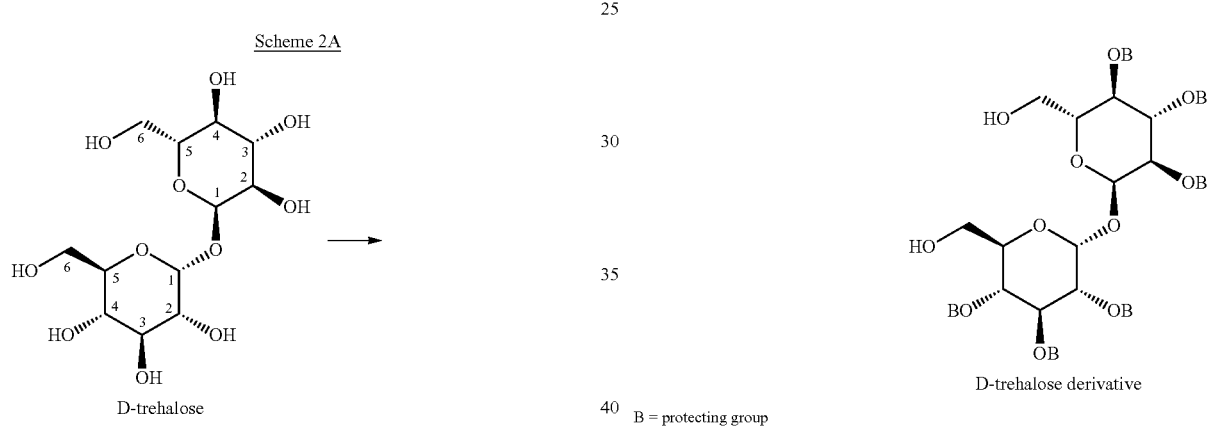

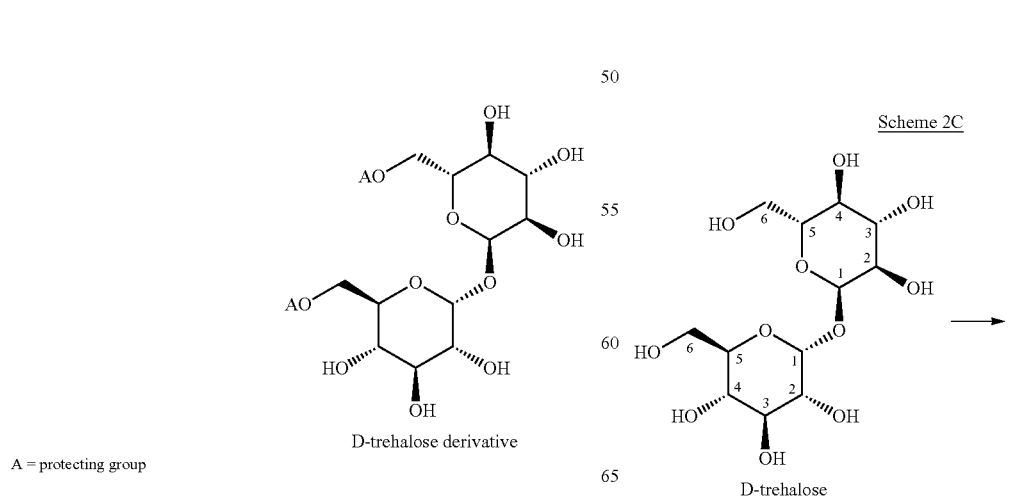

-continued

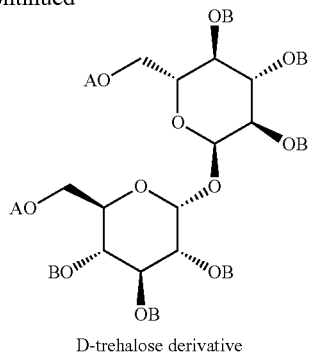

D-trehalose derivative

A = protection group
B = protecting group

In any embodiment, the primary hydroxyl groups at carbon 6 of each monosaccharide of the D-trehalose and secondary hydroxyl groups at carbon 4 of each monosaccharide of D-trehalose may be protected with acetal protecting groups to provide intermediate 0A-1 (e.g., Scheme 2D).

Scheme 2D

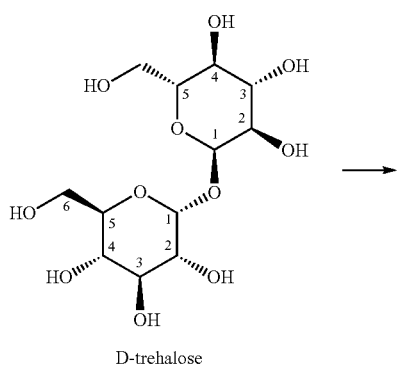

D-trehalose

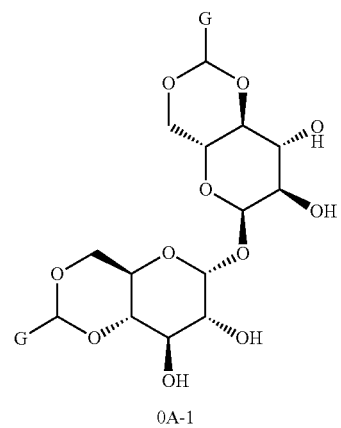

0A-1

G = remaining acetal structure

In any embodiment, the acetal protecting group (i.e., G in Scheme 2D) may have a structure of formula I:

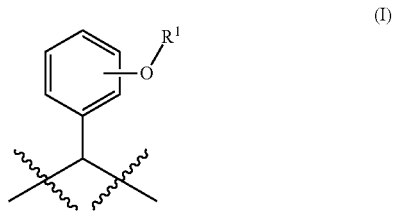

(I)

wherein $R^1$ is a halide (e.g., I, Br, Cl, or F), $NO_2$, or $C_1$-$C_6$ alkyl group. In some embodiments, $R^1$ may be a halide. In some embodiments, $R^1$ may be a chloride. In some embodiments, $R^1$ may be a $NO_2$. In some embodiments, wherein $R^1$ may be a $C_1$-$C_6$ alkyl group. In some embodiments, wherein $R^1$ may be a $C_1$-$C_3$ alkyl group. In some embodiments, wherein $R^1$ may be a $CH_3$. In some embodiments, the phenyl group may be ortho substituted. In some embodiments, the phenyl group may be meta substituted. In some embodiments, the phenyl group may be para substituted. In some embodiments, the acetal protecting group may have a structure of formula IA, wherein $R^1$ may be a $C_1$-$C_6$ alkyl group.

(IA)

In any embodiment, the method may further include one or more process steps after step (1) and before step (2). In any embodiment, the method may further include two or more process steps after step (1) and before step (2). In any embodiment, the method may further include three or more process steps after step (1) and before step (2).

In any embodiment, the method may further include protecting secondary hydroxyl groups at carbons 2 and 3 of the intermediate 0A-1 to provide intermediate 0A-2 (e.g., Scheme 2E). In any embodiment, the protecting group of the secondary hydroxyl groups at carbons 2 and 3 may be any hydroxyl protecting groups as listed above. In any embodiment, the protecting groups may be a benzyl protecting group.

Scheme 2E

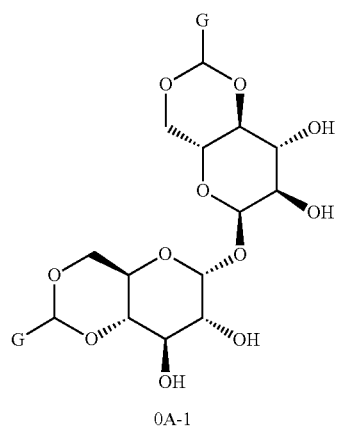

0A-1

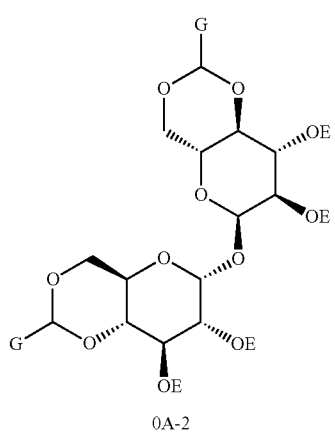

0A-2

E = protecting group or H
G = remaining acetal structure

In any embodiment, the method may further include removing the acetal protecting group of 0A-2 to provide the D-trehalose derivative (e.g., Scheme 2F).

Scheme 2F

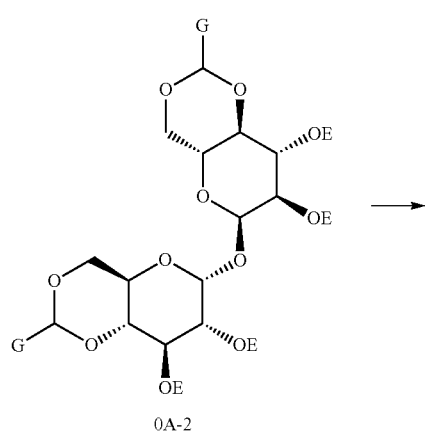

0A-2

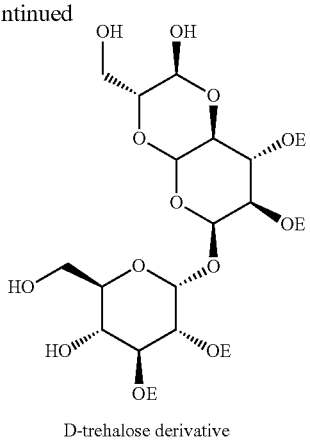

D-trehalose derivative

E = protecting group

In some embodiments, the method includes (2) protecting one or more primary and/or secondary hydroxyl groups of the D-trehalose or the D-trehalose derivative to provide an intermediate 1A. In any embodiment, the protecting may be accomplished with any of the hydroxyl protecting groups as listed above. In any embodiment, the protecting group may be a 4-nitrobenzenesulfonyl ("Ns") hydroxyl protecting group (e.g., Scheme 3A).

Scheme 3A

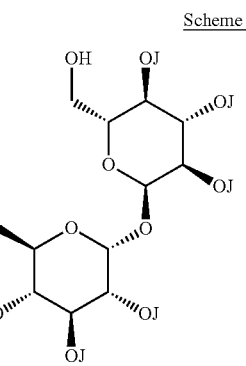

D-trehalose or
D-trehalose derivative

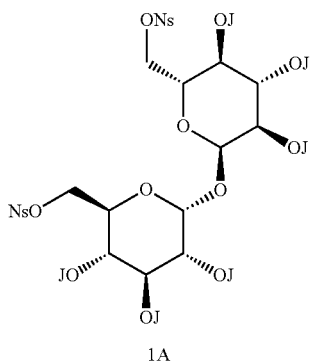

1A

J = protecting group or H

In some embodiments, the method includes (2) replacing the primary hydroxyl groups of the D-trehalose or the D-trehalose derivative with halides to provide an intermediate 1B. In any embodiment, the halides of the intermediate 1B include iodides (e.g., Scheme 3B).

Scheme 3B

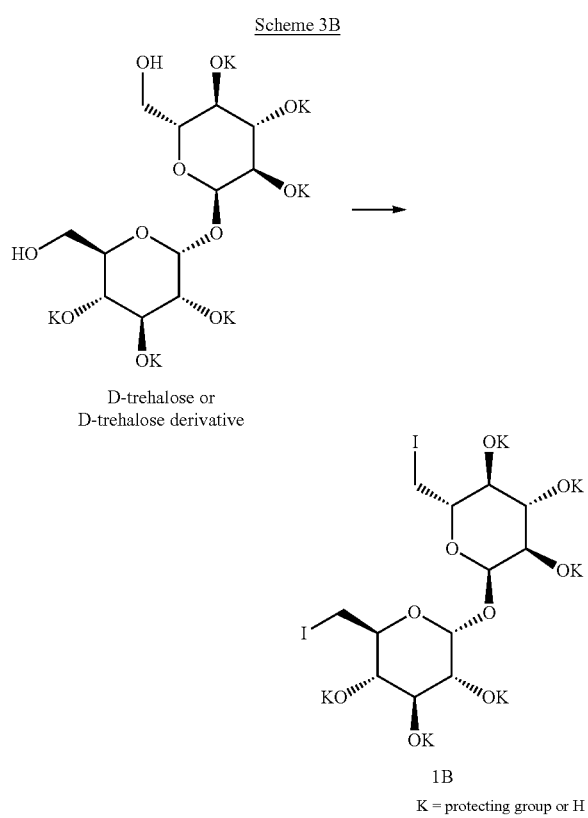

D-trehalose or
D-trehalose derivative

1B

K = protecting group or H

In any embodiment, the method may further include one or more process steps after step (2) and before step (3). In any embodiment, the method may further include two or more process steps after step (2) and before step (3). In any embodiment, the method may further include three or more process steps after step (2) and before step (3).

In any embodiment, the method may further include protecting the secondary hydroxyl groups at carbons 2, 3, and/or 4 of the intermediate 1B to provide intermediate 1B-1. The protecting may be accomplished with any of the hydroxyl protecting groups as listed above. In any embodiment, the protecting is conducted with an ester protecting group. In any embodiment, the ester protecting group may include an acetate protecting group.

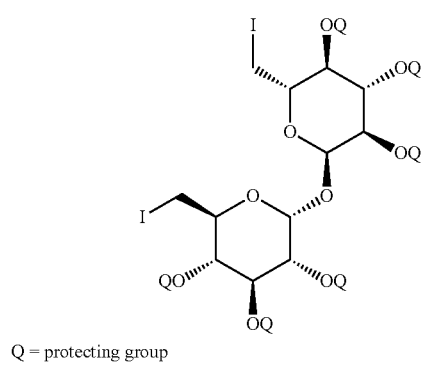

1B-1

Q = protecting group

In any embodiment, the method may further include converting the azides to protected amines. In any embodiment, the amine protecting group may be any amine protecting group listed above. In any embodiment, the amine protecting group may be an acetate protecting group.

In some embodiments, the method includes (3) replacing the primary hydroxyl protected groups with protected amines to provide intermediate 2. The groups protecting the amines may be any known amine protecting group. In any embodiment, the amine protecting group may be a carbobenzyloxy, p-methoxybenzyl carbonyl, t-butyloxycarbonyl, 9-fluorenylmethyloxycarbonyl, acetyl, benzoyl, benzyl, carbamate, p-methoxybenzyl, 3,4-dimethoxybenzyl, p-methoxyphenyl, tosyl, trichoroethyl chloroformate, phthaloyl, or sulfonamides. In any embodiment, the amine protecting group may be a benzyl protecting group. In any embodiment, the amine protecting group may be a phthaloyl protecting group.

In some embodiments, the method (3) includes replacing the primary hydroxyl protected groups with azides to provide intermediate 2. In any embodiment, the method includes (3) replacing the halides in intermediate 1B with protected amines or with azides to provide intermediate 2. Examples of intermediate 2 are provided below.

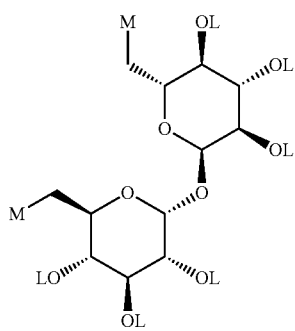

2 wherein L is a hydroxyl protecting (e.g., any hydroxyl protecting group disclosed herein) or H; and M is a protected amine or azide.

In any embodiment, the method may further include one or more process steps after step (3) and before step (4). In any embodiment, the method may further include two or more process steps after step (3) and before step (4). In any embodiment, the method may further include three or more process steps after step (3) and before step (4).

In some embodiments, (4) converting the intermediate 2 to DATH or a salt thereof may include removing all remaining protecting groups. In some embodiments, (4) converting the intermediate 2 to DATH or a salt thereof may include reducing all azides to amines. In some embodiments, (4) converting the intermediate 2 to DATH or a salt thereof may include removing all remaining protecting groups and reducing all azides to amines.

In any embodiment, the method may further include purifying one or more intermediate products and/or DATH. In any embodiment, the purifying may occur after converting, replacing, removing, and/or protecting processes. In any embodiment, the purifying may include filtration, centfrugation, chromatography, evaporation, liquid-liquid extraction, distillation, sublimation, crystallization, or a combination of two or more thereof. In any embodiment, the purifying may include crystallization. In any embodiment, crystallization may occur using one or more solvents. In any embodiment, the one or more solvents may include water, methanol, ethanol, isopropyl alcohol, acetonitrile, DMF, DMSO, or combinations of two or more thereof. In any embodiment, the one or more solvents may include water. In any embodiment, the one or more solvents may include water and ethanol. In any embodiment, the recrystallization of DATH may be conducted using water and ethanol. In any embodiment, the recrystallization of DATH may be conducted using water and ethanol at a ratio of about 5:1 to about 1:5 including about 3:1 to about 1:3, about 2:1 to about 1:2, about 1.5:1 to about 1:1.5, or about 1:1. In any embodiment, a second recrystallization of DATH may be conducted using water.

In any embodiment, the method may exclude use of trityl protecting groups. In any embodiment, the method may exclude use of tosyl protecting group. In any embodiment, the method may exclude use of trityl and tosyl protecting groups.

In another aspect, the present technology is direct to a method of producing DATH or a salt thereof including 1) optionally reacting D-trehalose with one or more protecting groups to provide a D-trehalose derivative; 2) reacting primary hydroxyl groups at carbon 6 of each monosaccharide of the D-trehalose or the D-trehalose derivative and 4-nitrobenzenesulfonyl-LG to provide intermediate 1A comprising 4-nitrobenzenesulfonyl hydroxyl protected groups, or reacting the primary hydroxyl groups of the D-trehalose or the D-trehalose derivative and a halogen to provide intermediate 1B comprising halide groups; (3) reacting the 4-nitrobenzenesulfonyl hydroxyl protected groups and potassium phthalimide, benzyl amine, ammonia, or $NaN_3$ to provide intermediate 2A, or reacting the halide groups and potassium phthalimide, benzyl amine, or $NaN_3$ to provide intermediate 2B; and (4) converting the intermediate 2A or the intermediate 2B to DATH or a salt thereof wherein LG represents a leaving group.

In some embodiments, the method includes (1) reacting D-trehalose with one or more protecting groups to provide a D-trehalose derivative. In any embodiment, the protecting group comprises a hydroxyl protecting group including any disclosed above. In any embodiment, the one or more protecting groups may include an acetal. In any embodiment, the reacting may include reacting the acetal and a primary hydroxyl group at carbon 6 and a secondary hydroxyl group at carbon 4 of each monosaccharide of the D-trehalose to provide intermediate 0A-1 (e.g., Scheme 2D). In any embodiment, the reacting the acetal and the primary hydroxyl group at carbon 6 and the secondary hydroxyl group at carbon 4 of each monosaccharide of the D-trehalose may further include adding camphorsulfonic acid and a solvent. In any embodiment, the solvent may include an organic solvent (e.g., polar aprotic solvent). In any embodiment, the solvent may include dimethylformamide ("DMF"), THF, acetonitrile, or a combination of two or more thereof. In any embodiment, the solvent may include DMF. In any embodiment, the reacting may be conducted at a temperature between about 25° C. and about 60° C. including about 30° C. and about 50° C., or about 35° C. and about 45° C. In any embodiment, the reacting may be conducted for a time range of about 10 to about 25 hours, about 12 hour to about 20 hours, or about 14 to about 18 hours. In any embodiment, the acetal protecting group may have a structure of formula I:

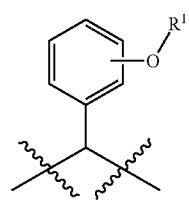

wherein $R^1$ is a halide (e.g., I, Br, Cl, or F), $NO_2$, or $C_1$-$C_6$ alkyl group. In some embodiments, $R^1$ may be a halide. In some embodiments, $R^1$ may be a chloride. In some embodiments, $R^1$ may be a $NO_2$. In some embodiments, wherein $R^1$ may be a $C_1$-$C_6$ alkyl group. In some embodiments, wherein $R^1$ may be a $C_1$-$C_3$ alkyl group. In some embodiments, wherein $R^1$ may be a $CH_3$. In some embodiments, the phenyl group may be ortho substituted. In some embodiments, the phenyl group may be meta substituted. In some embodiments, the phenyl group may be para substituted. In some embodiments, the acetal protecting group may have a structure of formula IA, wherein $R^1$ may be a $C_1$-$C_6$ alkyl group.

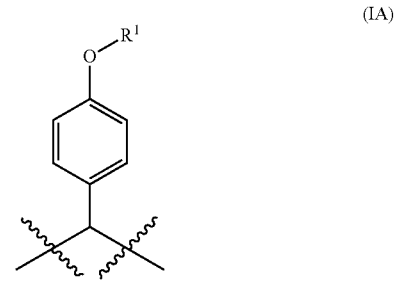

In any embodiment, the method may further include one or more process steps after step (1) and before step (2). In any embodiment, the method may further include two or more process steps after step (1) and before step (2). In any embodiment, the method may further include three or more process steps after step (1) and before step (2).

In any embodiment, the method may further include reacting secondary hydroxyl groups at carbons 2 and 3 of each monosaccharide of the intermediate 0A-1 and/or a hydroxyl protecting group to provide intermediate 0A-2 (e.g., Scheme 2E). In any embodiment, the hydroxyl protecting group may include any hydroxyl protecting group provided above. In any embodiment, the hydroxyl protecting group may include benzyl-LG, wherein LG represents a leaving group. In any embodiment, the hydroxyl protecting group may include benzyl chloride. In any embodiment, the reacting the secondary hydroxyl groups at carbons 2 and 3 of each monosaccharide of the intermediate 0A-1 and/or the hydroxyl protecting group may further include adding sodium hydroxide, tetra-n-butylammonium bromide, and/or a solvent. In any embodiment, the solvent may include a polar protic solvent (e.g., water and/or 2-methyltetrahydrofuran). In any embodiment, the reacting may be conducted at a temperature between about 40° C. and about 80° C. including about 50° C. and about 70° C., or about 55° C. and about 65° C. In any embodiment, the reacting may be conducted for a time range of about 2 to about 8 hours or about 3 to about 5 hours.

In any embodiment, the method may further include reacting the intermediate 0A-2 to remove the acetal protecting group to provide the D-trehalose derivative of step 1 (e.g., Scheme 2F). In any embodiment, the reacting may include adding a mixture of acetic acid and water to the intermediate 0A-2. In any embodiment, the reacting may be conducted at a temperature between about 50° C. and about 90° C. including about 60° C. and about 80° C., or about 65° C. and about 75° C. In any embodiment, the reacting may be conducted for a time range of about 1 to about 6 hours or about 2 to about 4 hours.

In some embodiments, the method includes (2) the reacting primary hydroxyl groups at carbon 6 of each monosaccharide of the D-trehalose or the D-trehalose derivative and 4-nitrobenzenesulfonyl-LG to provide intermediate 1A comprising 4-nitrobenzenesulfonyl hydroxyl protected groups. In any embodiment, the 4-nitrobenzenesulfonyl-LG may include 4-nitrobenzenesulfonyl chloride. In any embodiment, the reacting the D-trehalose or the D-trehalose derivative and the 4-nitrobenzenesulfonyl-LG further include adding 2,4,6-trimethylpyridine and a solvent. In any embodiment, the solvent may include an organic solvent (e.g., polar aprotic solvent). In any embodiment, the solvent may include methyl tert-butyl ether and/or tetrahydrofuran ("THF").

In some embodiments, the method includes (2) the reacting the primary hydroxyl groups of the D-trehalose or the D-trehalose derivative and a halogen (e.g., fluorine, chlorine, bromine, or iodine) to provide intermediate 1B comprising halide groups. In any embodiment, the halogen may include iodine. In any embodiment, the reacting the D-trehalose or the D-trehalose derivative and the halogen may further include adding imidazole, triphenylphosphine, a solvent, or a combination of two or more thereof. In any embodiment, the solvent may include an organic solvent (e.g., polar aprotic solvent). In any embodiment, the solvent may include dimethylformamide ("DMF"), THF, acetonitrile, or a combination of two or more thereof. In any embodiment, the solvent may include DMF. In any embodiment, the solvent may include THF. In any embodiment, the solvent may include acetonitrile. In any embodiment, the reaction may include about 1 to about 5 equivalents each of iodine, imidazole, and/or triphenylphosphine. In any embodiment, the reaction may include about 1.5 to about 4, about 2 to about 5 equivalents, about 2 to about 4 equivalents, about 2 to about 3 equivalents, or about 2.4 to about 2.9 equivalents each of iodine, imidazole, and/or triphenylphosphine. In any embodiment, the molar equivalents of iodine to imidazole may be about 5:1 to about 1:5, about 3:1 to about 1:3, about 1:2 to about 2:1, or about 1:1 to about 1:1. In any embodiment, the molar equivalents of iodine to triphenylphosphine may be about 5:1 to about 1:5, about 3:1 to about 1:3, about 1:2 to about 2:1, or about 1:1 to about 1:1. In any embodiment, the molar equivalents of imidazole to triphenylphosphine may be about 5:1 to about 1:5, about 3:1 to about 1:3, about 1:2 to about 2:1, or about 1:1 to about 1:1. In some embodiments, the reacting may include (A) pre-mixing the solvent and one or more of the reagents to provide a reagent mixture; and (B) adding the D-trehalose or the D-trehalose derivative to the reagent mixture. In any embodiment, the adding may be conducted at a temperature above about 50° C. such as between about 65° C. and about 100° C. or about 75° C. and about 90° C. In other embodiments, the reacting may include mixing the reagents and the D-trehalose or the D-trehalose derivative simultaneously. In any embodiment, the mixing may be conducted at a temperature between about 0° C. and about 50° C. including about 5° C. and about 40° C. or about 5° C. and about 20° C. In any embodiment, the reacting may be conducted for a time range of about 1 to about 8 hours or about 1 hour to about 5 hours.

In any embodiment, the method may further include one or more process steps after step (2) and before step (3). In any embodiment, the method may further include two or more process steps after step (2) and before step (3). In any embodiment, the method may further include three or more process steps after step (2) and before step (3).

In some embodiments, the method may further include reacting secondary hydroxyl groups at carbons 2, 3, and/or 4 of the intermediate 1B and a one or more protecting groups to provide intermediate 1B-1. In any embodiment, the one or more protecting groups may include any hydroxyl protecting group described above. In any embodiment, the one or more protecting groups may include an ester, an acyl halide, or an anhydride functional group. In any embodiment, the one or more protecting groups may include acetic anhydride. In any embodiment, the reacting may further include adding pyridine, 4-dimethylaminopyridine, triethylamine, or a combination of two more thereof. In any embodiment, the reacting may occur at a temperature between about 15° C. and about 30° C. or about 20° C. and about 25° C. In any embodiment, the reacting may occur for about 10 to about 30 hours, about 15 to about 25 hours, or about 18 to about 22 hours.

In some embodiments, the method includes (3) the reacting the 4-nitrobenzenesulfonyl hydroxyl protected groups and potassium phthalimide, benzyl amine, ammonia, or $NaN_3$ to provide intermediate 2A. In any embodiment, the reacting the 4-nitrobenzenesulfonyl hydroxyl protecting groups and the potassium phthalimide may further include adding a solvent (e.g., organic solvent). In any embodiment, the solvent may include N-methyl-2-pyrrolidone ("NMP"). In any embodiment, the reacting may be conducted at a temperature between about 50° C. and about 90° C. including between about 60° C. and about 80° C., or about 65° C. and about 75° C. In any embodiment, the reacting may be conducted for a time range of about 1 to about 12 days or about 5 to about 9 days.

In any embodiment, the reacting the 4-nitrobenzenesulfonyl hydroxyl protected groups and the benzyl amine may be conducted at a temperature between about 50° C. and about 80° C. including a temperature between about 55° C. and about 75° C. In any embodiment, the reacting the 4-nitrobenzenesulfonyl hydroxyl protected groups and the benzyl amine may be conducted for about 6 to about 12 hours or about 8 to about 10 hours. In any embodiment, the benzyl amine may be neat.

In any embodiment, the reacting the 4-nitrobenzenesulfonyl hydroxyl protected groups and the ammonia may include adding an organic solvent (e.g., polar protic). In any embodiment the solvent may include methanol. In any embodiment, the reacting may be conducted at a temperature between about 40° C. and about 80° C. including a temperature between about 50° C. and about 70° C. or about 55° C. and about 65° C. In any embodiment, the reacting may be conducted for about 20 to about 50 hours, about 25 to about 45 hours, or about 30 to about 40 hours.

In any embodiment, the reacting the 4-nitrobenzenesulfonyl hydroxyl protected groups and the $NaN_3$ may include adding an organic solvent (e.g., polar aprotic). In any embodiment the solvent may include NMP, DMF, or a combination thereof. In any embodiment, the reacting may be conducted at a temperature between about 30° C. and about 90° C. including a temperature between about 60° C. and about 80° C. or about 40° C. and about 60° C. In any embodiment, the reacting may be conducted for about 10 minutes to about 10 hours, about 10 to about 120 minutes, about 30 to about 90 minutes, or about 5 to about 8 hours.

In some embodiments, the method includes (3) the reacting the halide groups and potassium phthalimide, benzyl amine, or $NaN_3$ to provide intermediate 2B.

In some embodiments, the method may include the reacting the halide groups and the potassium phthalimide.

In some embodiments, the method may include the reacting the halide groups and the benzyl amine. In any embodiment, the reacting may be conducted at a temperature between about 25° C. and about 50° C. including between about 35° C. and about 45° C. In any embodiment, the reacting may be for about 6 to about 12 hours or about 8 to about 10 hours. In any embodiment, the benzyl amine may be neat.

In some embodiments, the method may include the reacting the halide groups and $NaN_3$. In any embodiment, the reacting may further include adding a solvent. In any embodiment, the solvent may include DMF, dimethyl sulfoxide ("DMSO"), methanol, water, or a combination of two or more thereof. In any embodiment, the reacting may be conducted at a temperature between about 50° C. and about 120° C. including between about 75° C. and about 100° C., about 80° C. and about 100° C., or about 70° C. and about 90° C. In any embodiment, the reacting may be for about 4 to about 30 hours, about 6 to about 22 hours, about 10 to about 20 hours, about 14 to about 22 hours, about 14 to about 24 hours, or about 16 to about 20 hours. In any embodiment, the reacting the halide groups and $NaN_3$ includes about 2 to about 10 molar equivalents $NaN_3$. In any embodiment, the reacting the halide groups and $NaN_3$ includes about 4 to about 8 molar equivalents $NaN_3$ including about 5 to about 7, about 2 to about 4, or about 2 to about 3 molar equivalents $NaN_3$. In any embodiment, the temperature may be between about 80° C. and about 100° C. or about 70° C. and about 90° C.; for about 6 to about 22 hours, about 10 to about 20 hours, about 14 to about 22 hours, or about 16 to about 20 hours; using about 5 to about 7, about 2 to about 4, or about 2 to about 3 molar equivalents $NaN_3$.

In some embodiments, the carbon 6 of each monosaccharide of the D-trehalose or the D-trehalose derivative may be substituted with an azide. In some embodiments, the reaction may use sodium azide. In some embodiments, the molar equivalents of azide may be about 2 to about 8, about 2.5 to about 7, or about 5 to about 7. In some embodiments, the temperature may about about 70° C. to about 120° C., about 80° C. to about 110° C., or about 85° C. to about 95° C.

In some embodiments, the method may further include reacting the azides with one or more protecting groups to provide protected amines. In any embodiment, the one or more protecting groups may include any amine protecting group as disclosed above. In any embodiment, the one or more protecting groups may include an ester, an acyl halide, or an anhydride functional group. In any embodiment, the one or more protecting groups may include acetic anhydride. In any embodiment, the reacting the azide and the secondary hydroxyl groups at carbons 2, 3, and/or 4 of the intermediate 1B with the one or more protecting groups may occur at the same time.

In any embodiment, the method includes (4) the converting the intermediate 2A or the intermediate 2B to 6,6'-diamino-6,6'-deoxy-trehalose or a salt thereof, the method including removing all remaining protecting groups, reducing azides to amines, or both. In some embodiments, the method includes removing all remaining protecting groups. In some embodiments, the method includes reducing azides to amines. In some embodiments, the method includes removing all remaining protecting groups and reducing azides to amines. In any embodiment, the removing all remaining protecting groups may occur first and the reducing azides to amines may occur second. In any embodiment, the reducing azides to amines may occur first and the removing all remaining protecting groups may occur second.

In any embodiment, the removing all remaining protecting groups may include reacting with $XOR^2$, wherein X is a cation and $R^2$ comprises H or $C_1$-$C_6$. In any embodiment, X may be $Na^+$ or $Li^+$ and $R^2$ may be H or $CH_3$. In any embodiment, the reacting may further include adding a solvent. In any embodiment, the solvent may include a polar protic solvent (e.g., water, methanol, or a combination thereof). In any embodiment, the reacting may occur at a temperature between about 20° C. and about 25° C. In any embodiment, the reacting may occur for between about 0.5 hours to about 3.5 hours.

In any embodiment, the reducing the azides to amines may include reacting the azides and $H_2$. In any embodiment, the reacting may further include adding a solvent and Pd/C or $Pd(OH)_2$. In any embodiment, the reacting may further include adding HCl. In any embodiment, the solvent may include a polar protic solvent (e.g., water, isopropanol, or a combination thereof). In any embodiment, the solvent may be a mixture of isopropanol and water (e.g., a ratio of about 1:3-about 3:1, about 1:2 to about 2:1, or about 1:2 to about 1:1) or water alone. In any embodiment, the reacting may occur at a temperature between about 20° C. and about 45° C. or about 20° C. and about 25° C. In any embodiment, the reacting may occur for between about 0.5 hours to about 5 hours or about 1 hour to about 2.5 hours. In any embodiment, the reacting may have an $H_2$ pressure of about 1 bar to about 8 bar including about 2 bar to about 6 bar, about 4 bar to about 6 bar, or about 2 bar to about 4 bar.

In any embodiment, the method may further include purifying one or more intermediate products and/or DATH. In any embodiment, the purifying may occur after one or more reacting steps. In any embodiment, the purifying may include filtration, centfrugation, chromatography, evaporation, liquid-liquid extraction, distillation, sublimation, crystallization, or a combination of two or more thereof. In any embodiment, the purifying may include crystallizing. In any embodiment, crystallization may occur using one or more solvents. In any embodiment, the one or more solvents may include water, methanol, ethanol, isopropyl alcohol, acetonitrile, DMF, DMSO, or combinations of two or more thereof. In any embodiment, the one or more solvents may include water. In any embodiment, the one or more solvents may include water and ethanol. In any embodiment, the recrystallization of DATH may be conducted using water and ethanol. In any embodiment, the recrystallization of DATH may be conducted using water and ethanol at a ratio of about 5:1 to about 1:5 including about 3:1 to about 1:3, about 2:1 to about 1:2, about 1.5:1 to about 1:1.5, or about 1:1. In any embodiment, a second recrystallization of DATH may be conducted using water.

In any embodiment, the method may exclude use of trityl protecting groups. In any embodiment, the method may exclude use of tosyl protecting group. In any embodiment, the method may exclude use of trityl and tosyl protecting groups.

In any embodiment disclosed herein, the methods may be conducted at an industrial scale. In any embodiment, the methods may be conducted on a scale in which greater than about 25 grams of DATH is produced. In any embodiment, the methods may be conducted on a scale in which greater than about 50 grams of DATH is produced. In any embodiment, the methods may be conducted on a scale in which greater than about 75 grams, about 100 grams, or about 110 grams of DATH is produced. In any embodiment, the overall yield of the method may be about 15% to about 40%. In any embodiment, the overall yield of the method may be about 18% to about 30%.

In any embodiment disclosed herein, the methods may produce DATH at a purity greater than 80%. In any embodiment disclosed herein, the methods may produce DATH at a purity greater than 90%. In any embodiment disclosed herein, the methods may produce DATH at a purity greater than 95%. In any embodiment disclosed herein, the methods may produce DATH at a purity greater than 99%.

In another aspect, provided herein is DATH produced by any method disclosed herein.

The present technology is also directed to intermediate products prepared during the method of producing DATH. In one aspect, the present technology is directed to a compound of formula II:

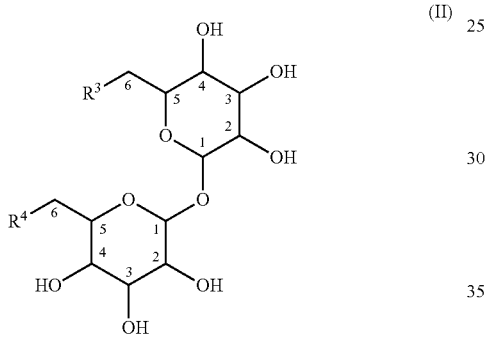
(II)

wherein $R^3$ and $R^4$ are independently selected from the group consisting of I or N3.

In any embodiment, the compound may be a compound of formula IIA:

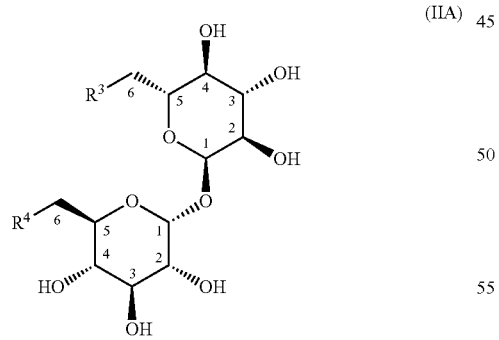
(IIA)

wherein $R^3$ and $R^4$ are independently selected from the group consisting of I or N3. In some embodiments, $R^3$ and $R^4$ may be I. In some embodiments, $R^3$ and $R^4$ may be N3.

The examples herein are provided to illustrate advantages of the present technology and to further assist a person of ordinary skill in the art with preparing or using the compounds of the present technology or salts, racemic mixtures or tautomeric forms thereof. The examples herein are also presented in order to more fully illustrate the preferred aspects of the present technology. The examples should in no way be construed as limiting the scope of the present technology, as defined by the appended claims. The examples can include or incorporate any of the variations, aspects or aspects of the present technology described above. The variations, aspects or aspects described above may also further each include or incorporate the variations of any or all other variations, aspects or aspects of the present technology.

EXAMPLES

Example 1: Synthesis of Intermediate 8

Scheme 4

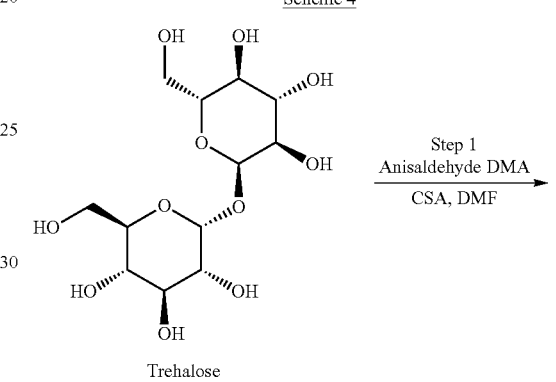

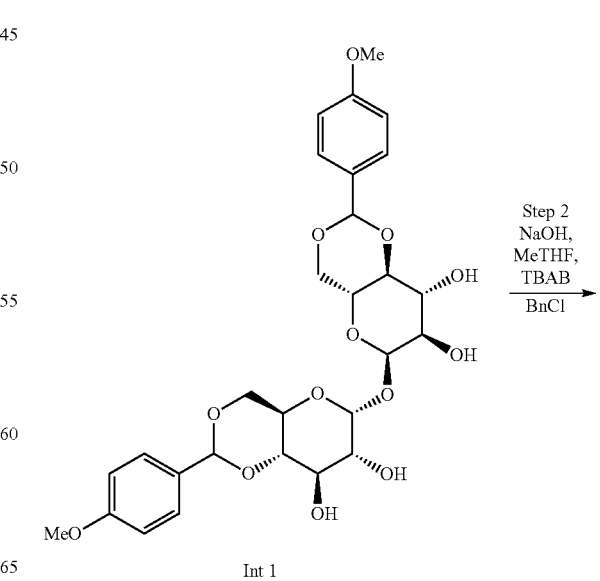

Int 1

26

Example 2: Synthesis of Intermediate 13

Scheme 5

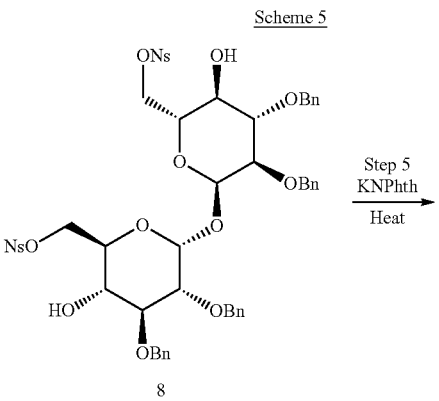

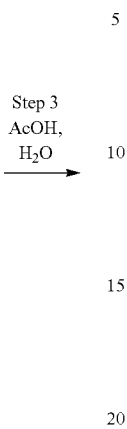

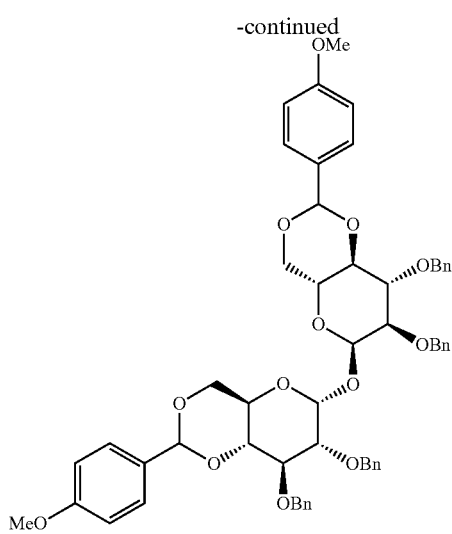

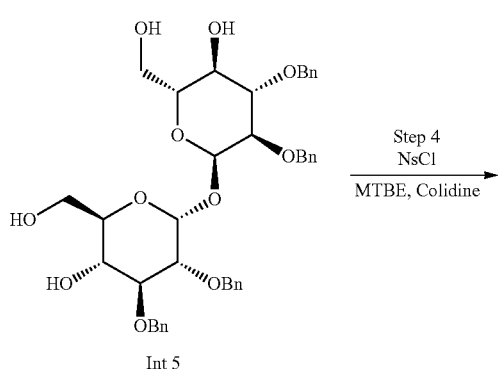

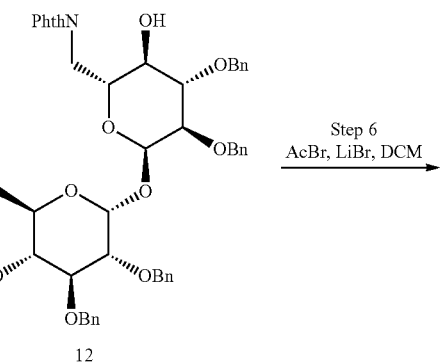

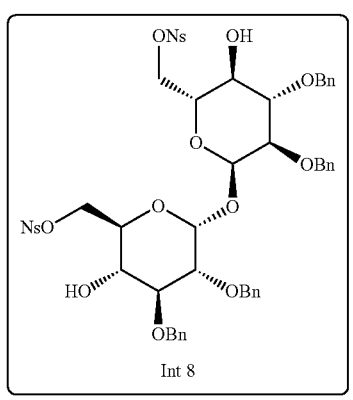

Scheme 4 describes the synthesis of intermediate 8. The hydroxyl groups at carbons 4 and 6 were protected with anisaldehyde to give intermediate 1. The remaining free hydroxyl groups were protected with a benzyl protecting group to give intermediate 3. The anisaldehyde protecting group was removed to give intermediate 5. The primary hydroxyl groups at carbon 6 were activated with a nosyl leaving group to give intermediate 8.

Scheme 5 describes the synthesis of intermediate 13. The nosyl protected primary hydroxyl groups were substituted with phthalimide to give intermediate 12. The benzyl protecting groups were replaced with acetate protecting groups and all secondary hydroxyl groups were protected with acetate to give intermediate 13.

Example 3: Synthesis of DATH from Intermediate 8

Scheme 6A

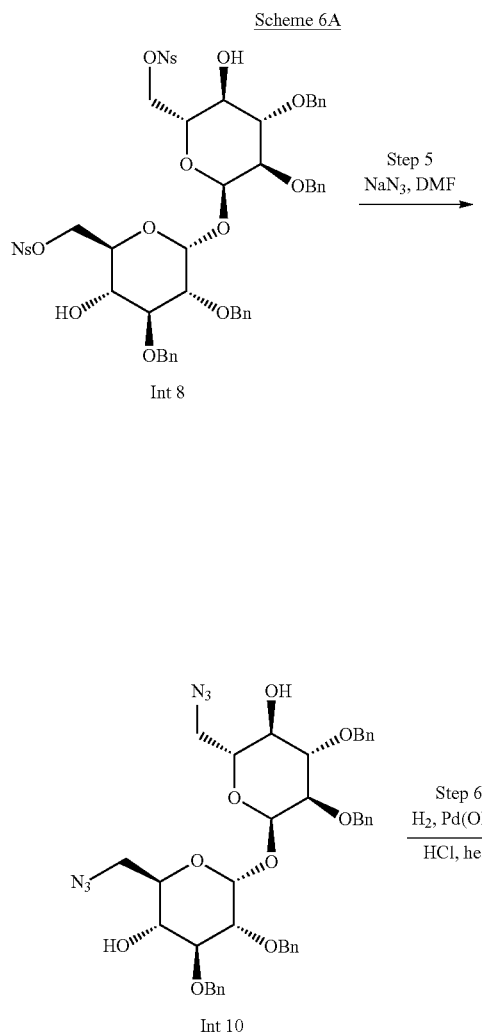

Scheme 6B

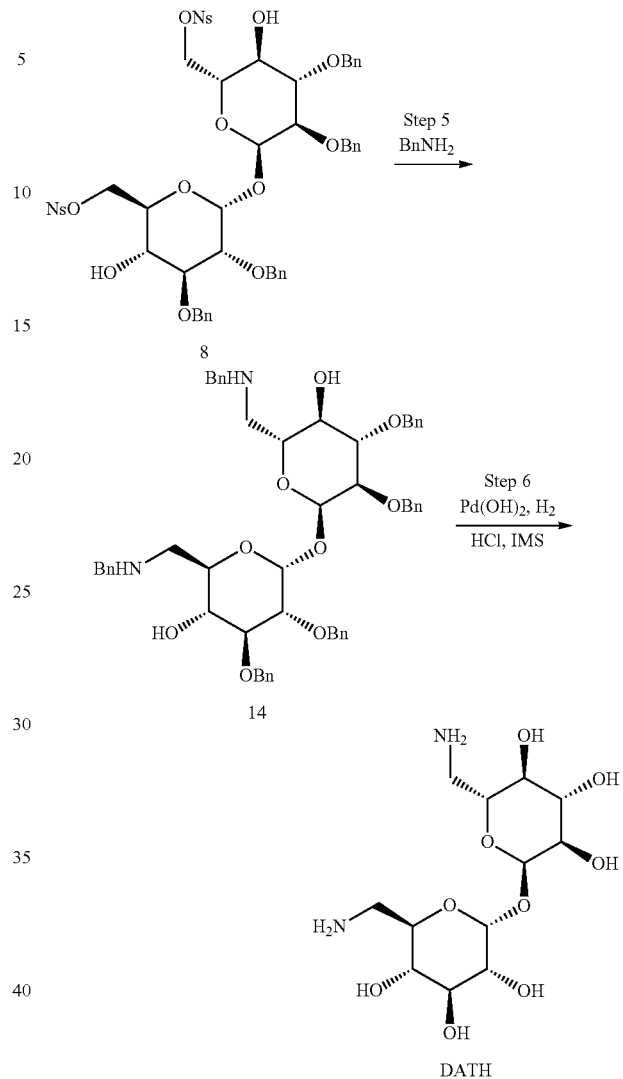

Scheme 6B describes the synthesis of DATH. The nosyl protected primary hydroxyl groups were substituted with benzyl amine to give intermediate 14. The protecting groups removed to provide DATH.

Scheme 6C

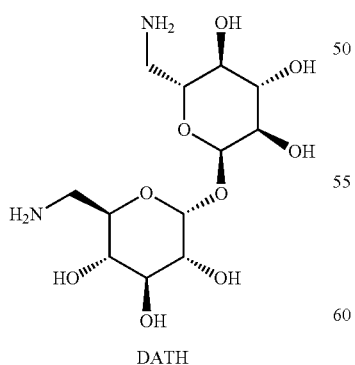

Scheme 6A describes the synthesis of DATH. The nosyl protected primary hydroxyl groups were substituted with azide to give intermediate 10. The azide was reduced and the protecting groups removed to provide DATH.

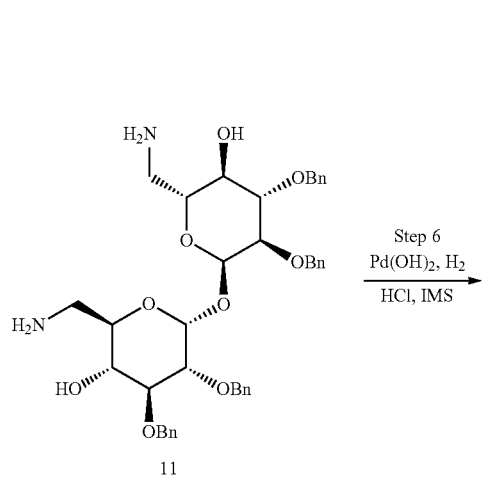
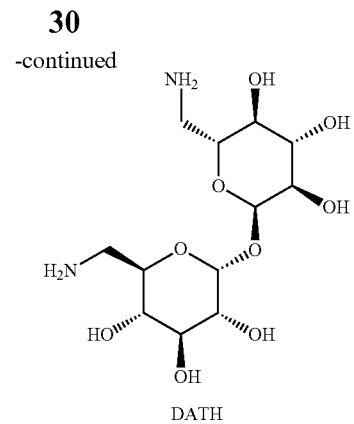
Scheme 6C describes the synthesis of DATH. The nosyl protected primary hydroxyl groups were substituted with ammonia to give intermediate 11. The protecting groups removed to provide DATH.
Example 4: Synthesis of DATH with Iodide, Azide, and Protected Amine Intermediates
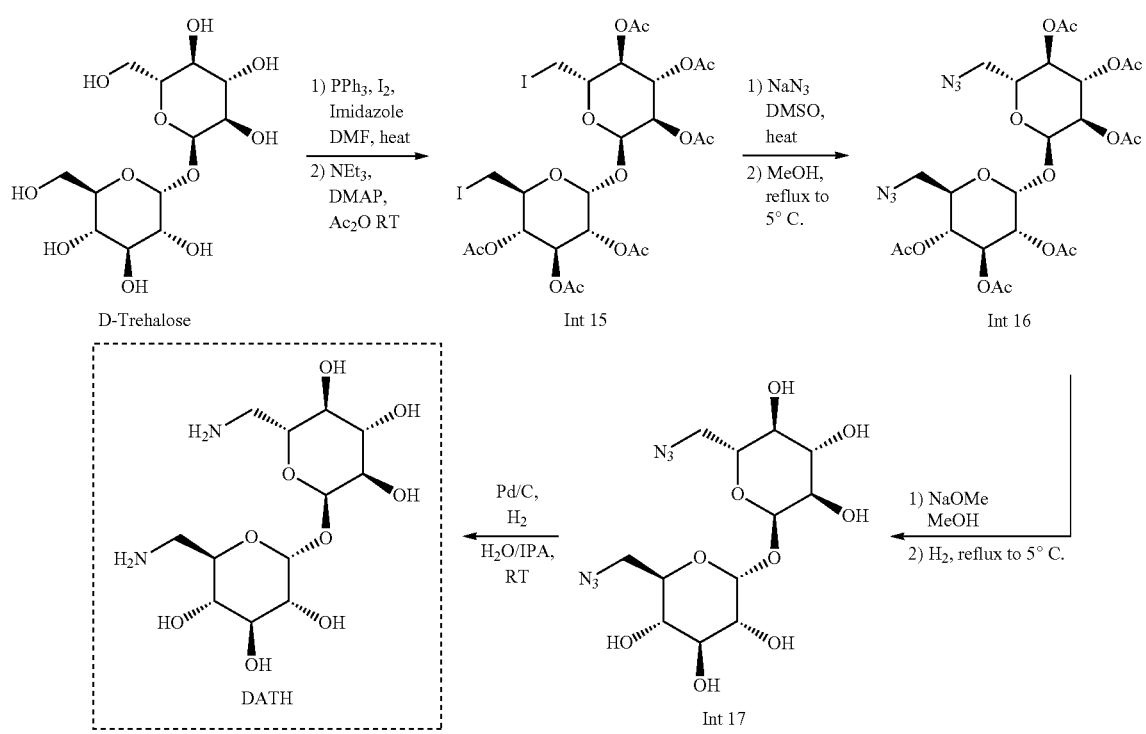

Scheme 7B

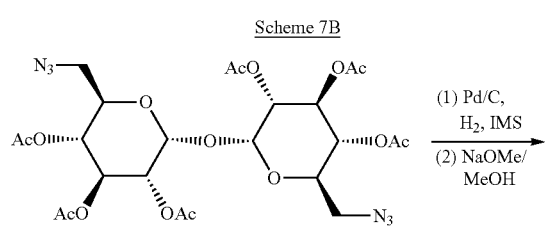

16

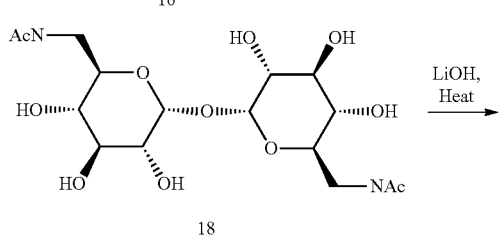

18

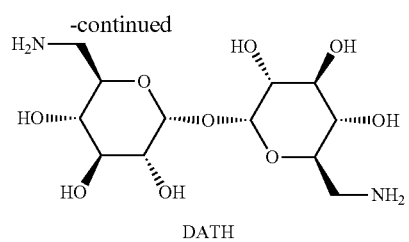

DATH

Schemes 7A and 7B describe the synthesis of DATH. The primary hydroxyl groups at carbon 6 were substituted with iodide followed by acetate protection of the secondary hydroxyl groups to give intermediate 15. The iodide was then substituted with azide to give intermediate 16. In Scheme 7A, the secondary hydroxyl groups of intermediate 16 were deprotected to provide intermediate 17 followed by reducing the azides to provide DATH. In Scheme 7B, the azides were reduced and the acetate protecting groups removed to provide intermediate 18. Due to acetyl migration, intermediate 18 was treated with lithium hydroxide to provide DATH.

Scheme 7C

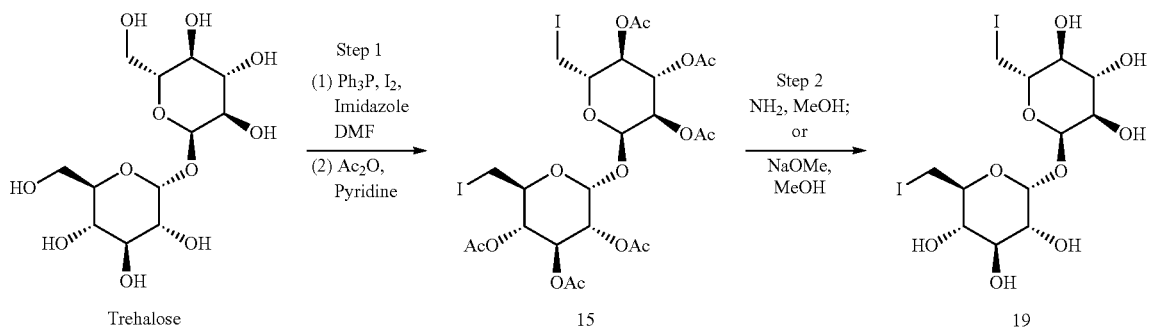

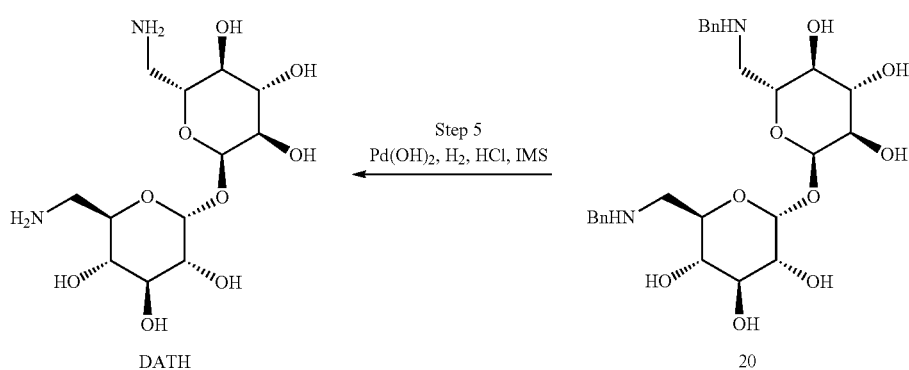

Scheme 7D

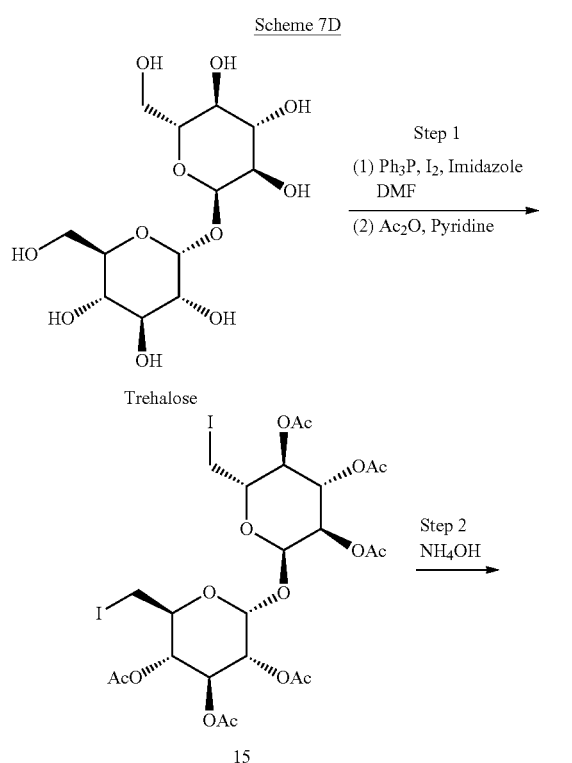

Trehalose

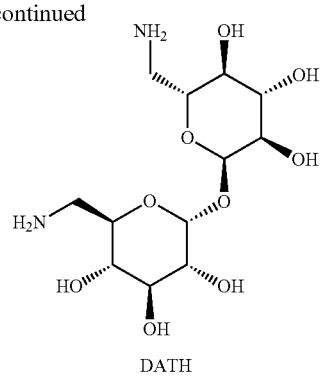

DATH

Schemes 7C and 7D also describe the synthesis of DATH following the synthesis of intermediate 15. Scheme 7C provides two procedures to produce intermediate 20. The first path substituting the iodides with benzyl amine and the second deprotecting the acetate groups prior to substituting the iodides with benzyl amine. The benzyl protecting group was then removed. In Scheme 7D, the iodide was substituted with ammonium.

Example 5: DATH Synthesis with Iodide and Azide Intermediates

Scheme 8

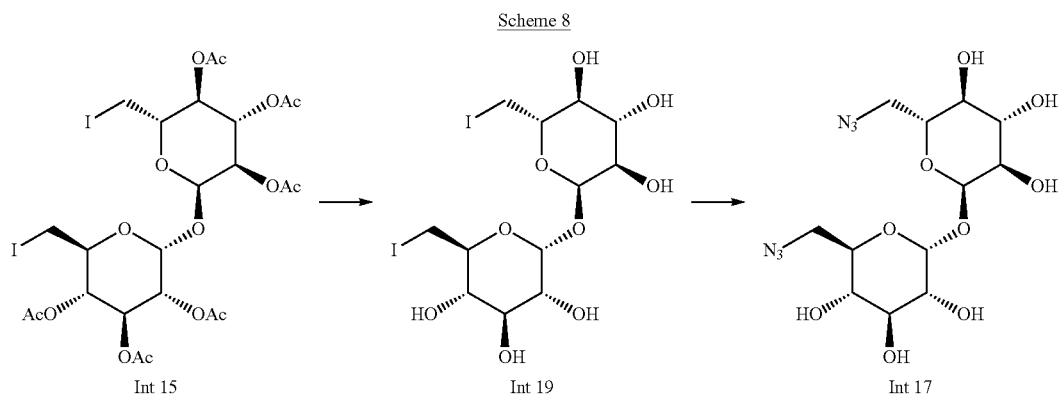

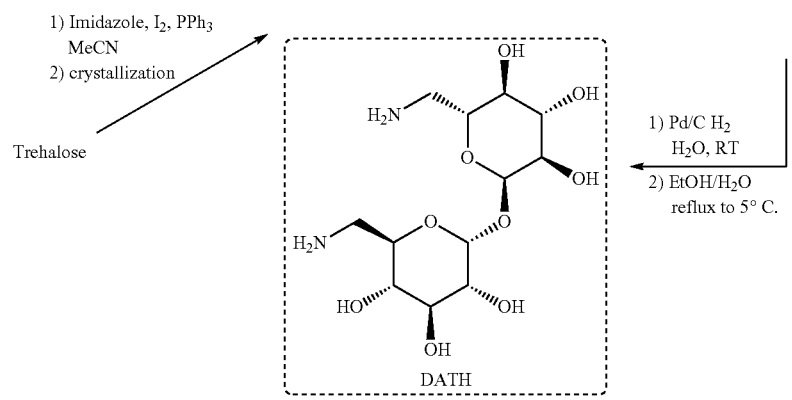

Scheme 8 describes the synthesis of DATH inverting the steps of acetate deprotection and azide substitution provided in Scheme 7A. The primary hydroxyl groups at carbon 6 were substituted with iodide followed by acetate protection of the secondary hydroxyl groups to give intermediate 15. The acetate protecting groups of the secondary hydroxyl groups were then removed to give intermediate 19. The iodide was then substituted with azide to give intermediate 17 followed by reducing the azides to provide DATH. While Schemes 7A and 8 describe protecting the secondary hydroxyl groups with acetate protecting groups, in alterative embodiments, the secondary hydroxyl groups may not be protected (e.g., provided in Scheme 8) or may be protected with other hydroxyl protecting groups known to person of ordinary skill in the art including those disclosed herein.

Example 6: Optimization of DATH Crystallization

The crystallization conditions of DATH were explored using varying solvent ratios provided in Table 1.

TABLE 1

Optimized DATH Crystallization

| DATH Sample | Crystallization Conditions | Yield | Purity |
| --- | --- | --- | --- |
| crude | | | 97.14% |
| A crystallized | 8.0 vol $H_2O$, 90° C. | 73% | 98.92% |
| B crystallized | 10.0 vol 1.5:1 $EtOH/H_2O$, 80° C. | 88% | 98.58% |
| C crystallized | 10.0 vol 1:1 $IPA/H_2O$, 80° C. | 82% | 98.69% |
| D crystallized | 11.0 vol 1:1 $MeOH/H_2O$, 65° C. | 77% | 98.56% |
| E crystallized | 11.0 vol 1:1 $MeCN/H_2O$, 80° C. | 84% | 98.40% |
| F crystallized | 10.0 vol 1:1 $DMF/H_2O$, 100° C. | 88% | 98.24% |
| G crystallized | 11.0 vol 1:1 $DMSO/H_2O$, 100° C. | 90% | 99.06% |

The crystallization conditions were explored using a crude sample of DATH, which contained 0.47% of impurity 1 and 2.39% of impurity 2. The original crystallization conditions used 8 volumes of water, which cleared all of impurity 1, but not all of impurity 2 and gave a yield of 73% (Sample A crystallized). Addition of EtOH (Sample B crystallized) to the crystallization solvent mixture improved the yield and the purging factor for impurity 2, but reduced the purging factor for impurity 1. A slight reduction of the amount of alcohol used (Sample C crystallized; it was determined EtOH could be replace with IPA) improved the purging factor for impurity 1 and reduced the purging factor for impurity 2, but did not change the yield. Other solvents tested (i.e., MeOH, MeCN, DMF, and DMSO) gave no noticeable improvement. It was therefore concluded that 1:1 EtOH/water was preferred for the crystallization of DATH as a compromise between yield and purging factor of the two identified impurities. If an additional recrystallization was required, water was used. The latter is especially useful for the purging of an unknown impurity with a retention time of 3.4 min above.

EQUIVALENTS

While certain embodiments have been illustrated and described, a person with ordinary skill in the art, after reading the foregoing specification, can effect changes, substitutions of equivalents and other types of alterations to the compounds of the present technology or salts, pharmaceutical compositions, derivatives, prodrugs, metabolites, tautomers or racemic mixtures thereof as set forth herein. Each aspect and embodiment described above can also have included or incorporated therewith such variations or aspects as disclosed in regard to any or all of the other aspects and embodiments.

The present technology is also not to be limited in terms of the particular aspects described herein, which are intended as single illustrations of individual aspects of the present technology. Many modifications and variations of this present technology can be made without departing from its spirit and scope, as will be apparent to those skilled in the art. Functionally equivalent methods within the scope of the present technology, in addition to those enumerated herein, will be apparent to those skilled in the art from the foregoing descriptions. Such modifications and variations are intended to fall within the scope of the appended claims. It is to be understood that this present technology is not limited to particular methods, reagents, compounds, compositions, labeled compounds or biological systems, which can, of course, vary. It is also to be understood that the terminology used herein is for the purpose of describing particular aspects only, and is not intended to be limiting. Thus, it is intended that the specification be considered as exemplary only with the breadth, scope and spirit of the present technology indicated only by the appended claims, definitions therein and any equivalents thereof.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

In addition, where features or aspects of the disclosure are described in terms of Markush groups, those skilled in the art will recognize that the disclosure is also thereby described in terms of any individual member or subgroup of members of the Markush group. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents (for example, journals, articles and/or textbooks) referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Other embodiments are set forth in the following claims, along with the full scope of equivalents to which such claims are entitled.

What is claimed is:

1. A method of producing 6,6'-diamino-6,6'-dideoxy-trehalose or a salt thereof, the method comprising:
   (1) optionally providing a D-trehalose derivative, comprising protecting and/or replacing one or more primary and/or secondary hydroxyl groups of D-trehalose to provide the D-trehalose derivative;
   (2) protecting one or more primary hydroxyl groups and one or more secondary hydroxyl groups of the D-trehalose or the D-trehalose derivative to provide intermediate IA or replacing the primary hydroxyl groups of the D-trehalose or the D-trehalose derivative with iodides to provide an intermediate IB;
   (3) replacing the primary hydroxyl protected groups of intermediate IA with protected amines to provide intermediate 2 or with azides to provide intermediate 2B; or
      (a) protecting secondary hydroxyl groups at carbons 2, 3, and/or 4 of the intermediate IB to provide intermediate IB-1, and (b) replacing the iodides of intermediate IB-1 with protected amines to provide intermediate 2 or with azides to provide intermediate 2B;
   (4) converting the azides, if present, of intermediate 2B into protected amines to provide intermediate 2; and
   (5) converting the intermediate 2 to 6,6'-diamino-6,6'-dideoxy-trehalose or a salt thereof;
   wherein the method excludes trityl, tosyl, or trityl and tosyl protecting groups.

2. The method of claim 1, wherein the hydroxyl protected groups of the intermediate 1A comprise 4-nitrobenzenesulfonyl hydroxyl protected groups.

3. The method of claim 1, comprising providing a D-trehalose derivative, wherein providing the D-trehalose derivative comprises protecting the primary hydroxyl groups at carbon 6 of each monosaccharide of the D-trehalose and the secondary hydroxyl groups at carbon 4 of each monosaccharide of the D-trehalose with acetal protecting groups to provide intermediate 0A-1.

4. The method of claim 3, wherein the acetal protecting groups have a structure of formula I:

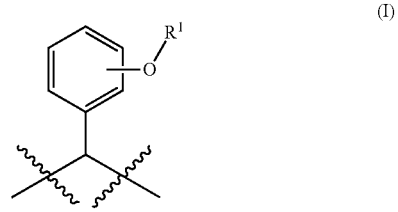

(I)

wherein $R^1$ is a $C_1$-$C_6$ alkyl group.

5. The method of claim 4, wherein $R^1$ is $CH_3$.

6. The method of claim 3, further comprising protecting secondary hydroxyl groups at carbons 2 and 3 of the intermediate 0A-1 to provide intermediate 0A-2.

7. The method of claim 6, wherein the protecting secondary hydroxyl groups at carbons 2 and 3 of the intermediate 0A-1 is conducted with a benzyl protecting group.

8. The method of claim 6, further comprising removing the acetal protecting groups to provide the D-trehalose derivative.

9. The method of claim 1, wherein the protected amines of (3) or (4) are protected by a benzyl or a phthaloyl protecting group.

10. The method of claim 1, wherein the protecting secondary hydroxyl groups at carbons 2, 3, and/or 4 of the intermediate 1B is conducted with an ester protecting group.

11. The method of claim 10, wherein the ester protecting group comprises an acetyl protecting group.

12. The method of claim 1, wherein the azides are converted into protected amines comprising acetyl protected amines.

13. The method of claim 1, wherein (5) comprises removing all remaining protecting groups.

14. The method of claim 1, further comprising purifying one or more times, wherein the purifying is conducted after converting, replacing, removing, and/or protecting.

15. The method of claim 14, wherein the purifying comprises crystallization.

* * * * *